United States Patent [19]

Babcock et al.

[11] Patent Number: 4,877,741

[45] Date of Patent: Oct. 31, 1989

[54] TREATMENT OF HUMAN PLASMA WITH BROWN RECLUSE SPIDER TOXIN TO EMULATE A LUPUS ANTICOAGULANT

[75] Inventors: James L. Babcock; David L. McGlasson, both of San Antonio, Tex.

[73] Assignee: The United States of America as represented by the Secretary of the Air Force, Washington, D.C.

[21] Appl. No.: 261,302

[22] Filed: Oct. 24, 1988

[51] Int. Cl.$^4$ .............................................. G01N 31/00
[52] U.S. Cl. ........................................ 436/8; 435/13; 436/69; 436/536
[58] Field of Search ........................ 436/69, 8; 435/13

[56] References Cited

U.S. PATENT DOCUMENTS 4,341,762 7/1982 Haast .
4,472,303 9/1984 Tabihara et al. .

OTHER PUBLICATIONS

Kurpiewski et al.–Chem. Abst. vol. 96 (1982) p. 47334j. Purification and Characterization of a Toxin from Brown Recluse Spider Venon Gland Extracts, James L. Babcock et al, Toxicon, vol. 19, No. 5, pp. 667–689, 1981.

Immunotoxicology of Brown Recluse Spider Venon, James L. Babcock et al, Toxicon, vol. 24, No. 8, pp. 783–790, 1986.

*Primary Examiner*—Sam Rosen
*Attorney, Agent, or Firm*—Fredric L. Sinder; Donald J. Singer

[57] ABSTRACT

A new method for improving the accuracy of blood tests for the presence of lupus anticoagulants and for blood factor deficiencies is disclosed. Brown recluse spiders are collected, their venon glands removed by microdissection and the active toxin extracted. The toxin is mixed with normal donor plasma in concentrations of about 3.5 $\mu$l/ml of toxin to plasma. The treated plasma successfully mimics human plasma having lupus anticoagulants. By using the treated plasma in blood tests and assays as a standardized control to which the results from tests on questioned blood plasma samples may be compared, the equipment and procedures for those tests may be calibrated and test results made more sensitive and reliable.

6 Claims, No Drawings

TREATMENT OF HUMAN PLASMA WITH BROWN RECLUSE SPIDER TOXIN TO EMULATE A LUPUS ANTICOAGULANT

RIGHTS OF THE GOVERNMENT

The invention described herein may be manufactured and used by or for the Government of the United States for all governmental purposes without the payment of any royalty.

BACKGROUND OF THE INVENTION

The present invention relates generally to medical testing methods, and more specifically to the use of a brown recluse spider (*Loxosceles reclusa*) toxin treated human plasma as a positive control, or standardized reference, for lupus anticoagulant blood tests.

Lupus anticoagulants are antibodies that interfere with blood coagulation, or clotting. Curiously, they are anticoagulants only in vitro, or outside the human body. In vivo, or inside the body, they act to increase the risk of thrombosis, or detrimental blood coagulation inside the heart, arteries, veins or capillaries. Lupus anticoagulants are found in the blood of many persons, and not merely in the blood of persons suffering from systemic lupus erythematosus, an inflammatory autoimmune disorder from which lupus anticoagulants derive their name. While persons having lupus anticoagulants present in their blood often show no adverse symptoms, a significant percentage of such persons will suffer from such complications as thrombosis, seizure disorders and, in women, spontaneous abortions.

Unfortunately, testing blood for the presence of lupus anticoagulants is very inexact. Present tests or assays used for detecting lupus anticoagulants, which generally test in vitro for various impaired coagulation indicators, can give misleading results from, for example, the presence of mild blood factor deficiencies. Blood factors are contributors to beneficial blood clotting and a deficiency in any one of many such factors will reduce clotting both in vivo and in in vitro tests so that they can produce, in vitro, the same test results as lupus anticoagulants. Vice versa, a mild blood factor deficiency may be misdiagnosed as the presence of a mild lupus anticoagulant. To most accurately test blood plasma samples for lupus anticoagulants, a standardized positive control is required for calibration and comparison of both testing equipment and technique. Because blood plasma with a lupus anticoagulant is not easily stored, and because patients with a lupus anticoagulant for obtaining blood samples are not always convenient, there is a need for a commercially available control plasma that accurately mimics the effects of a lupus anticoagulant in human plasma for laboratory testing. Without such a positive control, laboratory technicians cannot be certain that their testing for the presence of lupus anticoagulants is indeed performed in a manner consistent with expected results.

Treatments for complications from the presence in blood of correctly diagnosed lupus anticoagulants are generally successful. It is important, therefore, that accurate tests for the presence of lupus anticoagulants be available so that patients will receive the appropriate, and not a harmful, treatment for their illness.

It is, therefore, a principal object of the present invention to provide a method for performing accurate blood tests for the presence of lupus anticoagulants by the use of a positive control plasma that mimics the effects of a lupus anticoagulant in human plasma.

It is another object of the present invention to provide a method for preparing the positive control plasma that makes it readily available for commercial use.

A feature of the present invention is that its use of brown recluse spider toxin treated blood plasma can be extended for use as an all purpose abnormal control for defects of all the coagulation factors of the intrinsic clotting system. Its use will greatly increase the accuracy and sensitivity of all such tests.

Another feature of the present invention is that a very small amount of spider venom and the toxin produced from it will treat a large amount of blood plasma.

An advantage of the present invention is that its positive control plasma is prepared from normal donor plasma, reducing the possibility of HIV and hepatitis, and overcomes the limited availability of lupus anticoagulant plasma donors.

Another advantage of the present invention is that separate batches of the plasma can be made over time with equal and controlled potency. Plasma taken from even a single lupus anticoagulant donor will vary in potency from donation to donation.

A further advantage of the present invention is that it is a single abnormal control or standard. Other methods may require multiple controls.

SUMMARY OF THE INVENTION

The present invention provides a method for performing accurate blood tests for the presence of lupus anticoagulants by the use of a positive control plasma that mimics the effects of a lupus anticoagulant in human plasma. The unique discovery of the present invention is that blood plasma can be treated with toxin from brown recluse spider venom to make a positive control or standard for lupus anticoagulant blood plasma assays. The treated plasma can be successfully lyopholized (freeze-dried) and stored for use as a commercial product.

Accordingly, the present invention is directed to a method for improving the accuracy of blood tests for the presence of lupus anticoagulants and for blood plasma factor deficiencies, comprising the step of calibrating test procedures by comparing test results to results achieved using blood plasma treated with brown recluse spider toxin. The concentration of brown recluse spider toxin in the blood plasma may be about 3.4–3.8 μg/ml.

The invention also includes a method for preparing, storing and reconstituting for later use blood plasma treated with brown recluse spider toxin comprising the steps of freezing the treated blood plasma to about −70° C., lyopholizing the frozen treated blood plasma, storing the lyopholized treated blood plasma at freezer temperatures about −70° C. and reconstituting the treated blood plasma with distilled water.

The invention further includes a method for preparing, storing and reconstituting for later use blood plasma treated with brown recluse spider toxin comprising the steps of freezing the treated blood plasma to about −70° C., lyopholizing the frozen treated blood plasma, storing the lyopholized treated blood plasma at refrigerator temperatures about 2°–8° C. and reconstituting the treated blood plasma with distilled water.

DETAILED DESCRIPTION

The invention will be more clearly understood from a discussion of example typical blood test or assay procedures for the presence of lupus anticoagulants and various blood factor deficiencies, some of the problems encountered in obtaining accurate results and the solution provided by the present invention.

For example, activated partial thromboplastin time, or APTT, tests provide a time measure for clotting or coagulation ability of blood plasma. One method for determining whether or not a patient's in vitro clotting impairment is from the presence of lupus anticoagulants or from blood factor deficiencies is to first perform an APTT test on a sample of the patient's plasma searching for a slightly prolonged APTT of, for example, 40 seconds. The patient's plasma is then mixed 1:1 with known normal plasma and the test repeated. If the APTT corrects to, for example, 28 seconds, then the impairment is indicated to be from clotting factor deficiencies, the deficient factors having been provided by the known normal blood plasma. If the APTT does not correct, then the impairment is indicated to be from the presence of lupus anticoagulants. An example of the problems than can occur using this mixing test is that mild blood plasma factor deficiencies or weak lupus anticoagulants may or may not show dramatic correction times. By having a known lupus anticoagulant blood plasma, or reliable mimic, available, the test equipment and procedures can be calibrated to more clearly indicate what different test results mean. Additionally, the overall test procedure and calibration can be checked by seeing that reagents used in the test cause expected results with the lupus anticoagulant blood plasma mimic.

Another test where the commercial availability of a reliable mimic for blood plasma having a lupus anticoagulant will be valuable, particularly as a control, is in platelet neutralization procedures (PNP). These procedures involve looking for a degree of correction. A partial thromboplastin time test is performed for the questioned plasma diluted with saline solution. The saline is then replaced with a platelet concentrate which should overcome and correct any lupus anticoagulant. If the correction is greater than 5 seconds, then the presence of a lupus anticoagulant is indicated. If less than 5 seconds, then a factor deficiency might be indicated. In performing these tests, it is very easy to be misled by either a mild factor deficiency or a mild lupus anticoagulant. The use of a known standard lupus anticoagulant plasma as a positive control permits careful calibration so that a battery of tests can be run to increase sensitivity and confidence that a correct diagnosis has been made and that the appropriate course of treatment will be prescribed.

Those with skill in the art of the invention will readily see that the availability of a standard blood plasma which reliably mimics the presence of a lupus anticoagulant in blood plasma will be a valuable aid as a control in a great variety of other medical tests. Such other tests include, but are not limited to, prothrombin time (PT), Kaolin clotting time (KCT), KCT dilution, tissue thromboplastin inhibition tests and Russell's viper venom time tests.

To prepare the toxin treated blood plasma as a mimic for blood plasma having a lupus anticoagulant, brown recluse spiders are collected during warm summer months from buildings in Arkansas or Texas. Their venom glands are removed by microdissection and buffered extracts prepared by maceration followed by centrifugation. The supernatant (floating on top) fluid is purified by ion exchange chromatography to a single protein.

A background description of the preparation of the purified lethal toxins from the spider venom using standard biochemical techniques may be found in Babcock et al., *Toxicon*, Vol. 17, No. 5, pp. 677-689 (1981), which paper is hereby incorporated by reference and copies included with this application as filed. The articles discusses the presence of possibly two or three separate proteins being present in the described purified lethal toxin. Later research indicates that it is more likely a single protein with different charge forms.

Blood is drawn from normal human donors with sodium citrate vacutainer blood collecting tubes with a blood to anticoagulant ratio of 9:1. The citrated blood is centrifuged at 1300g for 30 minutes. The supernatant plasma is then separated and placed in plastic 12×75mm aliquots in 1.0 ml amounts. Spider toxin in a citrate buffer is added to the one ml aliquots to achieve a final concentration of toxin to plasma of about 3.5 μg/ml. The treated plasma is incubated at 37° C. for 10 min and placed on ice. A blank tube with just the buffer added to a second tube of plasma is processed in the same manner. A prothrombin time and an APTT is run to check the effect of the toxin. The buffer treated plasma should give results within normal laboratory limits. The toxin treated plasma should give a prothrombin time that is upper limit normal with a prolonged APTT.

The plasma is then transferred to lyopholizing vials in 1.0 ml aliquots and frozen at −70° C. for one hour. The lyopholizing vials with the treated plasmas are placed on a lyopholizing freezer dryer for 16 hours for lyopholization to take place. The lyopholized plasma vials are than capped, sealed and stored at 2°-8° C. refrigeration until ready for use. Recent experimentation shows that greatly increased storage times may be obtained by storage at −70° C. freezer temperatures.

When ready to use for testing, the plasma is reconstituted with 1.0 ml of distilled water and then allowed to stand for 20 minutes after gentle mixing.

The brown recluse toxin treated plasma can be used for testing like any commercial plasma standard or control. Additionally, the buffer treated plasma can be used, if so desired, as a control to the toxin treated plasma.

To perform the invention, the treated plasma is reconstituted and used as a control to calibrate the desired blood coagulation tests.

The disclosed method for improving the accuracy of blood tests for the presence of lupus anticoagulants and for blood factor deficiencies successfully demonstrates the use of brown recluse spider toxin treated blood plasma as a reliable mimic and improved substitute for blood plasma having lupus anticoagulants. Though the disclosed use is specialized, it will find application in other areas of medical testing where substitutes for naturally occurring substances are required as standardized controls. While it is a novel way to make a blood plasma having lupus anticoagulant-like properties, its example and teachings can be applied toward finding other substances which both mimic and are more readily available than other important reagents.

It is understood that certain modifications to the invention as described may be made, as might occur to one with skill in the field of the invention, within the intended scope of the claims. Therefore, all embodiments contemplated have not been shown in complete detail. Other embodiments may be developed without departing from the spirit of the invention or from the scope of the claims.

We claim:

1. A method for preparing, storing and reconstituting for later use blood plasma treated with brown recluse spider toxin comprising the steps of:
   (a) freezing blood plasma treated with brown recluse spider toxin to about −70° C.;
   (b) lyopholizing the frozen treated blood plasma;
   (c) storing the lyopholized treated blood plasma at freezer temperatures about −70° C.; and,
   (d) reconstituting the treated blood with distilled water for use as a positive control for blood tests for the presence of lupus anticoagulants and for blood factor deficiencies.

2. A method for preparing, storing and reconstituting for later use blood plasma treated with brown recluse spider toxin comprising the steps of:
   (a) freezing blood plasma treated with brown recluse spider toxin to about −70° C.;
   (b) lyopholizing the frozen treated blood plasma;
   (c) storing the lyopholized treated blood plasma at refrigerator temperatures about 2°–8° C.; and,
   (d) reconstituting the treated blood plasma with distilled water for use as a positive control for blood tests for the presence of lupus anticoagulants and for blood factor deficiencies.

3. A method for improving the accuracy of blood tests for the presence of lupus anticoagulants and for blood factor deficiencies, comprising the steps of:
   (a) providing a supply of blood plasma treated with brown recluse spider toxin;
   (b) providing a supply of questioned blood plasma for testing;
   (c) performing a first set of blood tests using the brown recluse spider toxin treated blood plasma;
   (d) performing a second set of blood tests using the questioned blood plasma; and,
   (e) comparing the results of the second set of blood tests to the results of the first set using the results of the first set as a positive control for blood having present a lupus anticoagulant.

4. The method according to claim 3, wherein the concentration of brown recluse spider toxin in the treated blood plasma is about 3.4–3.8 μg/ml.

5. A method for improving the accuracy of blood tests for the presence of lupus anticoagulants and for blood factor deficiencies, comprising the steps of:
   (a) providing a supply of blood plasma treated with brown recluse spider toxin;
   (b) performing the blood tests using the brown recluse spider toxin treated blood plasma; and,
   (c) using the test results of step (b) as positive control values for blood having present a lupus anticoagulant.

6. The method according to claim 5, wherein the concentration of brown recluse spider toxin in the blood plasma is about 3.4–3.8 μg/ml.

* * * * *